(12) United States Patent
Basener (10) Patent No.: US 11,456,059 B2
(45) Date of Patent: Sep. 27, 2022

(54) SYSTEM, APPARATUS AND METHOD FOR HIERARCHICAL IDENTIFICATION, MULTI-TIER TARGET LIBRARY PROCESSING, AND TWO-STAGE IDENTIFICATION

(71) Applicant: Geospatial Technology Associates LLC, Barboursville, VA (US)

(72) Inventor: William F. Basener, Advance Hills, VA (US)

(73) Assignee: Geospatial Technology Associates LLC, Barboursville, VA (US)

( * ) Notice: Subject to any disclaimer, the term of this patent is extended or adjusted under 35 U.S.C. 154(b) by 659 days.

(21) Appl. No.: 16/108,737

(22) Filed: Aug. 22, 2018

(65) Prior Publication Data

US 2019/0065696 A1 Feb. 28, 2019

Related U.S. Application Data

(60) Provisional application No. 62/548,795, filed on Aug. 22, 2017.

(51) Int. Cl.
*G16C 20/20* (2019.01)
*G06F 17/18* (2006.01)
(Continued)

(52) U.S. Cl.
CPC ............ *G16C 20/20* (2019.02); *G01J 3/2823* (2013.01); *G01N 21/31* (2013.01); *G06F 17/18* (2013.01); *G06K 9/6215* (2013.01); *G06K 9/6282* (2013.01); *G06V 20/13* (2022.01); *G16B 35/00* (2019.02); *G16C 20/60* (2019.02);
(Continued)

(58) Field of Classification Search
CPC .................. G01J 3/2823; G01N 21/31; G06K 2009/4657; G06K 2209/21
See application file for complete search history.

(56) References Cited

U.S. PATENT DOCUMENTS 5,978,497 A * 11/1999 Lee ..................... G01N 15/1475
382/133
6,008,492 A 12/1999 Slater et al.
(Continued)

OTHER PUBLICATIONS

Ogorzala, David R., etaL, Gas Plume Species Identification by Regression Analyses, Algorithms and Technologies for Multispectral, Hyperspectral, and Ultraspectral Imagery X, Proc of SPIE ,vol. 5425, pp. 583-591. (Year: 2004).*

(Continued)

*Primary Examiner* — Michael J Dalbo
(74) *Attorney, Agent, or Firm* — Williams Mullen; Thomas F. Bergert (57) ABSTRACT

Embodiments of a system, method and apparatus incorporate two-stage identification of targets in hyperspectral image analysis. In various embodiments, unmixing is employed that integrates F-test and model averaging approaches. Further, a multi-tier target library process provides an improvement in the spectra that can be used to detect target materials and spectra that can be used for unmixing in identification. Additionally, the hierarchical identification of the present disclosure combines probabilities from model averaging to generate target identifications simultaneously at multiple levels of specificity.

20 Claims, 5 Drawing Sheets

(51) Int. Cl.

| | |
|---|---|
| G01J 3/28 | (2006.01) |
| G06K 9/62 | (2022.01) |
| G16B 35/00 | (2019.01) |
| G16C 20/60 | (2019.01) |
| G01N 21/31 | (2006.01) |
| G06V 20/13 | (2022.01) |
| G16C 20/70 | (2019.01) |
| G16C 20/90 | (2019.01) |
| G01N 21/17 | (2006.01) |
| G06V 10/58 | (2022.01) |
| G06V 20/10 | (2022.01) |

(52) U.S. Cl.
CPC ...... *G01N 2021/1793* (2013.01); *G06V 10/58* (2022.01); *G06V 20/194* (2022.01); *G06V 2201/07* (2022.01); *G16C 20/70* (2019.02); *G16C 20/90* (2019.02)

(56) References Cited

U.S. PATENT DOCUMENTS

| | | | |
|---|---|---|---|
| 6,665,438 | B1 | 12/2003 | Lin |
| 6,940,999 | B2 | 9/2005 | Lin |
| 6,958,466 | B1 | 10/2005 | Stein |
| 7,020,326 | B1 | 3/2006 | Hsu |
| 8,897,489 | B2 | 11/2014 | Basener |
| 9,076,039 | B2 | 7/2015 | Halper et al. |
| 2005/0286770 | A1* | 12/2005 | Hirata .................. G06K 9/0063 382/191 |
| 2006/0158647 | A1 | 7/2006 | Yao |
| 2010/0329512 | A1 | 12/2010 | Nam et al. |
| 2014/0185864 | A1* | 7/2014 | Halper .................. G06K 9/0063 382/103 |
| 2014/0321697 | A1* | 10/2014 | Robinson ........... G06K 9/00536 382/103 |
| 2016/0313184 | A1* | 10/2016 | Owechko ............. G06K 9/6219 |

OTHER PUBLICATIONS

Pei-jun Du, Kun Tan, Hong-jun Su, Feature extraction for target identification and image classification of OMIS hyperspectral image, Mining Science and Technology (China), vol. 19, Issue 6, 2009, pp. 835-841, ISSN 1674-5264, (Year: 2009).*

S. Stankevich, V. Levashenko and E. Zaitseva, "Fuzzy decision tree model adaptation to multi- and hyperspectral imagery supervised classification," The International Conference on Digital Technologies 2013, 2013, pp. 198-202, doi:10.1109/DT.2013.6566311. (Year: 2013).*

Kumar, Hierarchical Fusion of Multiple Classifiers for Hyperspectral Data Analysis, Pattern Analysis & Applications (2002)5:210-220. (Year: 2002).*

Basener, William F., et al., A Dynamical Systems Algorithm for Clustering in Hyperspatial Imagery, SPIE Algorithms & Technology for Multispectral, Hyperspectral, and Ultraspectral Imaging XIV, (2008).

Paglieroni, D.W., et al., Optimal Segmentation Strategy for Compact Representation of Hypersprectral Image Cubes, U.S. Department of Energy-Lawrence Livermore National Laboratory, (2000).

Basener, William F., An Automated Method for Identification and ranking of hyperspectral target detections, Proc SPIE vol. 8048, Algorithms and Technologies for Multispectral, Hyperspectral, and Ultraspectral Imagery XVII, (2011).

Basener, William F., Ensemble Learning and Model Averaging for Material Identification in Hyperspectral Imagery, Algorithms for Multispectral, Hyperspectral, and Ultraspectral Imagery XXIII, Proceedings of SPIE, Aneheim, CA: SPIE, (2017).

Bergman, Steven M., The Utility of Hyperspectral Data to Detect and Discriminate Actual and Decoy Target Vehicles, Calhoun, Institutional Archive of the Naval Postgraduate School (1996), Monterey, CA.

Burr, Tom, et al., Chemical Identification Using Bayesian Model Selection, Spring Research Conference—Section on Physical & Engineering Sciences (SPES), pp. 338-342, (2002).

Pogorzala, David R., et al., Gas Plume Species Identification by Regression Analyses, Algorithms and Technologies for Multispectral, Hyperspectral, and Ultraspectral Imagery X, Proc of SPIE, vol. 5425, pp. 583-591, (2004).

Stevenson, Brian, et al., The Civil Air Patrol ARCHER Hyperspectral Sensor System, Airborne Intelligence, Surveillance, Reconnaissance (ISR) Systems and Applications II, Proc SPIE vol. 5787, pp. 17-28, (2005).

Stellmen, Christopher M., et al., Dark HORSE 2 Quick-Look Report: Real-time Detection of Military Ground Targets Using and Infrared Hyperspectral Imaging Sensor, Naval Research Laboratory, Advanced Concepts Branch Optical Sciences Division, (1999).

Manolakis, Dimitris, et al., Hyperspectral Image Processing for Automatic Target Detection Applications, Lincoln Lab Journal, pp. 79-115, (2003).

Borghys, Dirk, et al., Supervised Classification of Hyperspectral Images Using a Combination of Spectral and Spatial Information, Royal Military Academy, Signal & Image Centre, Renaissancelaan 30, B-1000, Brussels, Belgium.

Shimabukuro, Y.E., et al., The Least-Squares Mixing Models to Generate Fraction Images Derived from Remote Sensing Multispectral Data, IEEE Transactions on Geoscience and Remote Sensing, vol. 29, No. 1, pp. 16-22, (1991).

Harris Corporation, (n.d.), Material Identification, Find and Interpret the Unseen, (2015).

Higbee, Shawn, A Bayesian Approach to Identification of Gaseous Effluents in Passive LWIR Imagery, Rochester Institute of Technology, (2009).

Cipar, John J., et al., Comparison of Endmember Extraction Techniques, Algorithms and Technologies for Multispectral, Hyperspectral, and Ultraspectral Imagery VIII, Proc SPIE vol. 4725, (2002).

Raftery, Adrian E., et al., Bayesian Model Averaging for Linear Regression Models, Journal of the American Statistical Association, vol. 92, pp. 179-191, (1997).

Eismann, Michael T., Strategies for Hyperspectral Target Detection in Complex Background Environments, Air Force Research Laboratory, Wright-Patterson AFB, IEEE (2006).

George, Edward I., The Variable Selection Problem, University of Texas-Austin (2000).

Kalman, L.S., et al., Classification and Material Identification in an Urban Environment Using HYDICE Hyperspectral Data, Proc SPIE vol. 3118, Imaging Spectrometry III (1997).

Keshava, N., A Survey of Spectral Unmixing Algorithms, Lincoln Lab Journal, vol. 14, pp. 55-78, (2003).

Polikar, R., Ensemble Based Systems in Decision Making, IEEE Circuits and Systems Magazine, Third Q 2006.

Hirsh, R.F., The Riddle of the Gaseous Nebulae, The History of Science Society, The University of Chicago Press Journals, Isis, vol. 70, No. 2, pp. 197-212, (1979).

Eismann, Michael T., et al., Automated Hyperspectral Target Detection and Change Detection from an Airborne Platform: Progress and Challenges, The Airforce Research Laboratory, Space Computer Corporation, (2010).

Smith, Randall B., Introduction to Hyperspectral Imaging, MicroImages, Inc., (2012).

Kabacoff, Robert I., Multiple (Linear) Regression, https://www.statmethods.neUstats/regression.html, (2017).

Amini, Shahram M., et al., Bayesian Model Averaging in R, Journal of Economic and Social Measurement vol. 36 Iss. 4, (2011).

Olsen, R.C., et al., Target Detection in a Forest Environment Using Spectral Imagery, Proc of SPIE, (1997).

Basner, Bill, et al., A Detection-Identification Process With Geometric Target Detection and Subpixel Spectral Visualization, Rochester Institute of Technology, Digital Imaging and Remote Sensing Laboratory IEEE, (2011).

Thompson, David R., et al., Sparse Superpixel Unmixing for Exploratory Analysis of Crism Hyperspectral Images, Jet Propulsion Laboratory, California Institute of Technology, (2009).

Stein, D., Material Identification and Classification in Hyperspectral Imagery Using the Normal Compositional Model, Proc SPIE vol.

(56) References Cited

OTHER PUBLICATIONS

5093, Algorithms and Technologies for Multispectral, Hyperspectral, and Ultraspectral Imagery IX, (2003).
Manolakis, D., et al., Is There a Best Hyperspectral Detection Algorithm? Proc SPIE 7334, Algorithms and Technologies for Multispectral, Hyperspectral, and Ultraspectral Imagery XV, (2009).
Hoeting, Jennifer A., et al., Bayesian Model Averaging: A Tutorial, Statistical Science vol. 14, No. 4, pp. 382-417, (1999).

* cited by examiner

SYSTEM, APPARATUS AND METHOD FOR HIERARCHICAL IDENTIFICATION, MULTI-TIER TARGET LIBRARY PROCESSING, AND TWO-STAGE IDENTIFICATION

CROSS-REFERENCE TO RELATED APPLICATIONS

The present application claims priority to U.S. provisional application No. 62/548,795, filed Aug. 22, 2017, entitled, "System, Apparatus and Method for Hierarchical Identification, Multi-Tier Target Library Process, and Two-Stage Identification".

TECHNICAL FIELD

Embodiments of the present disclosure independently and collectively improve material identification in hyperspectral imagery.

BACKGROUND AND SUMMARY

Hyperspectral imagery is a form of digital imagery in which each pixel contains not just the standard visual three wavelength colors (red, green, blue), but hundreds of wavelengths enabling spectroscopy of chemical constituents within each pixel. The two main modalities for hyperspectral imaging are Visible Near-Infrared Short Wave Infrared (VNIRSWIR, 0.5-2.5 microns) and Long Wave Infrared (LWIR, 8-14 microns). In VNIRSWIR data, the spectra is a measurement of sunlight reflecting off solid objects, while in LWIR the spectrum is either emitted by a solid or emitted by and attenuated through a gas cloud. Historically, research in LWIR hyperspectral imagery evaluation focused more on identification of individual chemical species present in a gas plume drawing on previous use of imaging spectroscopy in astronomy, while the VNIRSWIR research community was less focused on identification as a primary goal.

In the early years of hyperspectral image processing, there was an emphasis on target detection—the detection of pixels in an image that are on a designated target material. An early effort to build an automated computer processor for such detection focused on applying target detection to images as they were collected directly from a sensor. In this effort, imagery was georectified and displayed in a viewer with detected targets. Targets were detected with a constant false alarm rate (CFAR) threshold, and the user could compare the pixel spectra manually to library spectra. As with all target detection methods, the software suffered from a high false alarm rate.

By comparison to target detection, material identification in hyperspectral imagery is the process of determining the material(s) present in a pixel in an image. While the goal of target detection is to determine the few pixels out of a full image (or images) that contain pre-designated target material, the goal in material identification is to determine the material(s) present in a single pixel or group(s) of pixels on an object.

Material identification in hyperspectral imaging is often done by comparing the measured spectrum to a library of known spectra and determining the library spectra and abundances that combine to give the observed spectrum. A spectrum for a material is a vector of measured intensities of light across different wavelengths from the material. The light may be emitted by the material or reflected off the material, although in either case the spectrum is a function of the chemical structure of the material. Because each pixel in an image generally contains more than one material, the measured pixel spectrum will be a linear combination of the spectra of the materials present in the pixel. Determining the spectra is typically done using libraries of known materials present in the pixel treated as a (linear) mixture. This linear unmixing problem is known in statistical analysis and addressed later herein.

An understood goal in material identification in hyperspectral imagery is to determine with a high level of certainty and specificity which material(s) are present in a pixel. Some algorithms seek to determine the best set of materials that are present in the pixel, while others seek to determine the presence or absence of a single material of interest, as described, for example, in U.S. Pat. No. 9,076,039 to Halper and Basener, the disclosure of which is incorporated by reference herein in its entirety.

A fundamental problem in hyperspectral imagery analysis is that library spectra often do not capture the desired level of specificity for an application, nor do they capture the level of specificity available in the data. For example, it might be desirable to have a single class for trees, or the user might wish to subdivide trees into deciduous and evergreens, or further into individual species. Or, possibly the user prefers to have a single vegetation class. The term "resolution" can be used to describe the degree to which an algorithm separates materials into different classes. For example, an identification method that subdivides trees into individual species has high resolution whereas a clustering that keeps a single vegetation class has a low resolution.

Another problem in hyperspectral imagery is that no specific approach to statistical regression for linear unmixing is ideal. There are many variations of statistical regression. The most common statistical regression method for material identification is a least squares linear regression, often using a stepwise or similar search for a reduced best model, where the 'best' model is chosen using any of a number of statistical model selection metrics including the adjusted $R^2$, Mallow's Cp, or an F-test score. The F-test, which is the most common metric used in hyperspectral imaging, is a statistical metrics that compares the goodness of fit for a linear mixture model to a null model. A more recent alternative approach to statistical regression is to use model averaging, which compares among the most likely models instead of picking a single best model.

The F-test approach and the model averaging approach each have specific strengths and weaknesses. The F-test methods are good at picking a best model and determining if that model is a likely 'true' model, but are not effective at distinguishing between correlated confuser materials. It is not unusual to get a high F-test score even though the materials in the model are similar to, but not the same as, the target materials. Methods using model averaging are good at distinguishing between correlated confusers, but do not provide a rigorous estimate of whether the materials are present. Model averaging methods require a complete library of all possible materials, which is never achievable. It is not unusual to get a high probability for a target class in model averaging when no target material is present. Methods relying on the F-test tend to have a low false alarm rate but have trouble distinguishing target materials from close confusers, while methods relying on model averaging are effective at distinguishing between difficult confusers, but have a tendency to false alarm on anomalous materials that are not present in the identification library.

These two different approaches are really two different schools of thought on regression—the "Pick a Winner"

school that tries to find a single best model and the "Model Averaging" school that tries to compete best models against each other. The weaknesses of each are inherent to the theoretical approaches; the F-test is based only on the best-fit model, whereas the model averaging assumes that the materials present in the pixel must be in the predetermined identification libraries.

Among other things, the present disclosure provides a system, method and apparatus for two-stage identification, wherein the unmixing integrates the F-Test and model averaging approaches, providing the best features of both methods. Further, the multi-tier target library as part of the present disclosure provides an improvement in the spectra that can be used to detect target materials and spectra that can be used for unmixing in identification. Additionally, the hierarchical identification of the present disclosure combines probabilities from model averaging to generate much more detailed information about the target material by providing identification simultaneously at multiple levels of specificity.

DETAILED DESCRIPTION

The terminology used herein is for the purpose of describing particular embodiments only and is not intended to be limiting of the approach. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1:
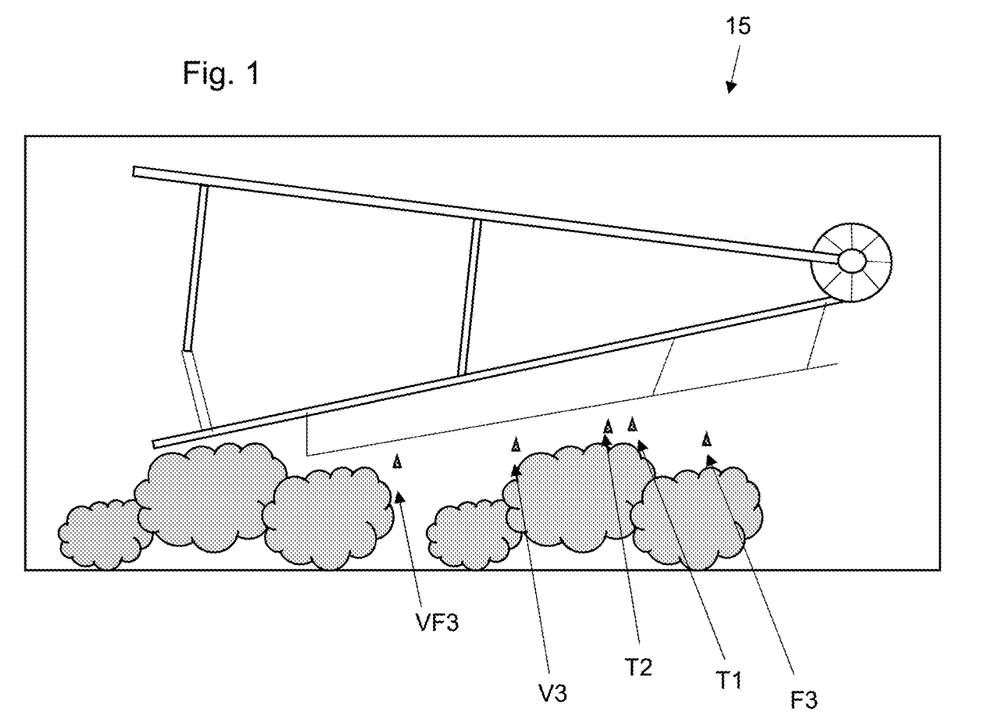
FIG. 1 is a drawing representing a sample hyperspectral image.

According to the present disclosure, hierchical identification identifies the material(s) present in a pixel at multiple levels of resolution simultaneously. For example, identification of the material in a pixel may determine vegetation versus non-vegetation. If the material is deemed vegetation, further identification is provided to determine whether the vegetation is deciduous or evergreen. If deciduous, for example, a specific species is provided if possible from the data. This is done in a hierchical manner to meet the needed level of specificity (i.e., resolution) and at the maximum resolution possible given the imagery. Two sample results are provided in the image 15 of FIG. 1, which shows a drawing representing a forest with selected targets, with explanation below.

Figure 2A:
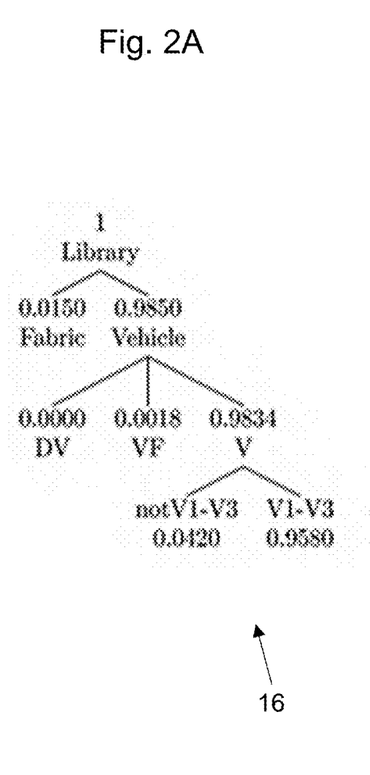
FIGS. 2A and 2B are exemplary hierarchies with object probabilities as determined in accordance with embodiments of the present disclosure.

In the diagram 16 of FIG. 2A, the class identification tree for V3 is shown. At each branch in the tree, the possible subclasses are listed with probabilities ordered from least likely to most likely. In the diagram 18 of FIG. 2B above, the class identification tree for VF3 is shown. At each branch in the tree, the possible subclasses are listed with probabilities ordered from least likely to most likely.

We first consider the vehicle V3 and FIG. 2A. At the highest level, we assume with probability 1 that the spectra for the selected object is in the library. This is a basic assumption intrinsic to model averaging. At the next level, it is determined that the probability that the target is a fabric is 0.0150 while the probability that the target is a vehicle is 0.9850. Continuing down the tree, we see that there is approximately a 95% probability that this target is in the class V1-V3, which is the most specific class assignment that can be made with this library.

Figure 2B:
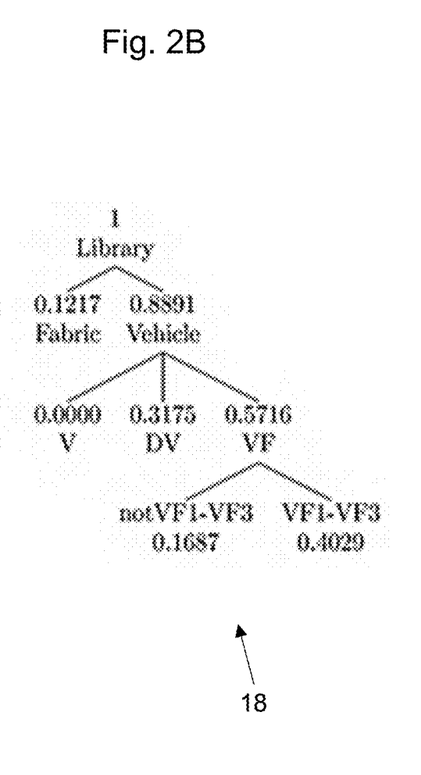

The class identification tree for vehicle VF3 is shown in FIG. 2B. Observe that for VF3, it was possible to determine with confidence that this object is a vehicle, and either a DV or VF class vehicle. After that, the designation becomes less certain. We can tell that this object is about twice as likely to be a VF than DV, and if it is a VF then it is twice as likely to be a VF1-VF3 than one of the other vehicles. But this designation within the vehicle classes cannot be made with as much certainty as was possible with V3 in FIG. 2A.

The spectra in a spectral library for hierarchical classification must have a category for multiple levels. An example of the multi-level categories are shown in Table 1 that could have been used to classification in FIGS. 2A and 2B. It will be appreciated that embodiments of the library can be much larger.

TABLE 1

| Spectrum | Level 1 | Level 2 | Level 3 |
|---|---|---|---|
| F1_1 | Fabric | | |
| F1_2 | Fabric | | |
| F1_3 | Fabric | | |
| DV1_1 | Vehicle | DV | |
| DV1_2 | Vehicle | DV | |
| DV1_3 | Vehicle | DV | |
| V1_1 | Vehicle | V | V1-V3 |
| V1_2 | Vehicle | V | V1-V3 |
| V1_3 | Vehicle | V | V1-V3 |
| V2_1 | Vehicle | V | V1-V3 |
| V2_2 | Vehicle | V | V1-V3 |
| V2_3 | Vehicle | V | V1-V3 |
| V3_1 | Vehicle | V | V1-V3 |
| V3_2 | Vehicle | V | V1-V3 |
| V3_3 | Vehicle | V | V1-V3 |
| V4_1 | Vehicle | V | not V1-V3 |
| V4_2 | Vehicle | V | not V1-V3 |
| V4_3 | Vehicle | V | not V1-V3 |
| VF1_1 | Vehicle | VF | VF1-VF3 |
| VF1_2 | Vehicle | VF | VF1-VF3 |
| VF1_3 | Vehicle | VF | VF1-VF3 |
| VF2_1 | Vehicle | VF | VF1-VF3 |
| VF2_2 | Vehicle | VF | VF1-VF3 |
| VF2_3 | Vehicle | VF | VF1-VF3 |
| VF3_1 | Vehicle | VF | VF1-VF3 |
| VF3_2 | Vehicle | VF | VF1-VF3 |
| VF3_3 | Vehicle | VF | VF1-VF3 |
| VF4_1 | Vehicle | VF | not VF1-VF3 |
| VF4_2 | Vehicle | VF | not VF1-VF3 |
| VF4_3 | Vehicle | VF | not VF1-VF3 |
| VF5_1 | Vehicle | VF | not VF1-VF3 |
| VF5_2 | Vehicle | VF | not VF1-VF3 |
| VF5_3 | Vehicle | VF | not VF1-VF3 |

For each node in the hierarchical identification tree, the probability for the node is the sum of all models in the model averaging that have a spectrum with the label for the node. For example, the identification in FIG. 2A, the sum of the probabilities of all models that contained a spectrum with a Fabric label in Level 1 (F1_1, F1_2, and F1_3) was 0.0150, while the sum of probabilities for all models containing spectra that had a Vehicle label in Level 1 (all other spectra) was 0.980. At level 2, the sum of probabilities of all models that contain a spectrum with a DV label was 0.000, with a VF label was 0.0018, and with a V label was 0.9834. In this manner, the probabilities for all possible labels at all levels are computed, and the hierarchical identification tree following the highest probability at each level is provided to the user as shown in FIGS. 2A and 2B.

Figure 3:
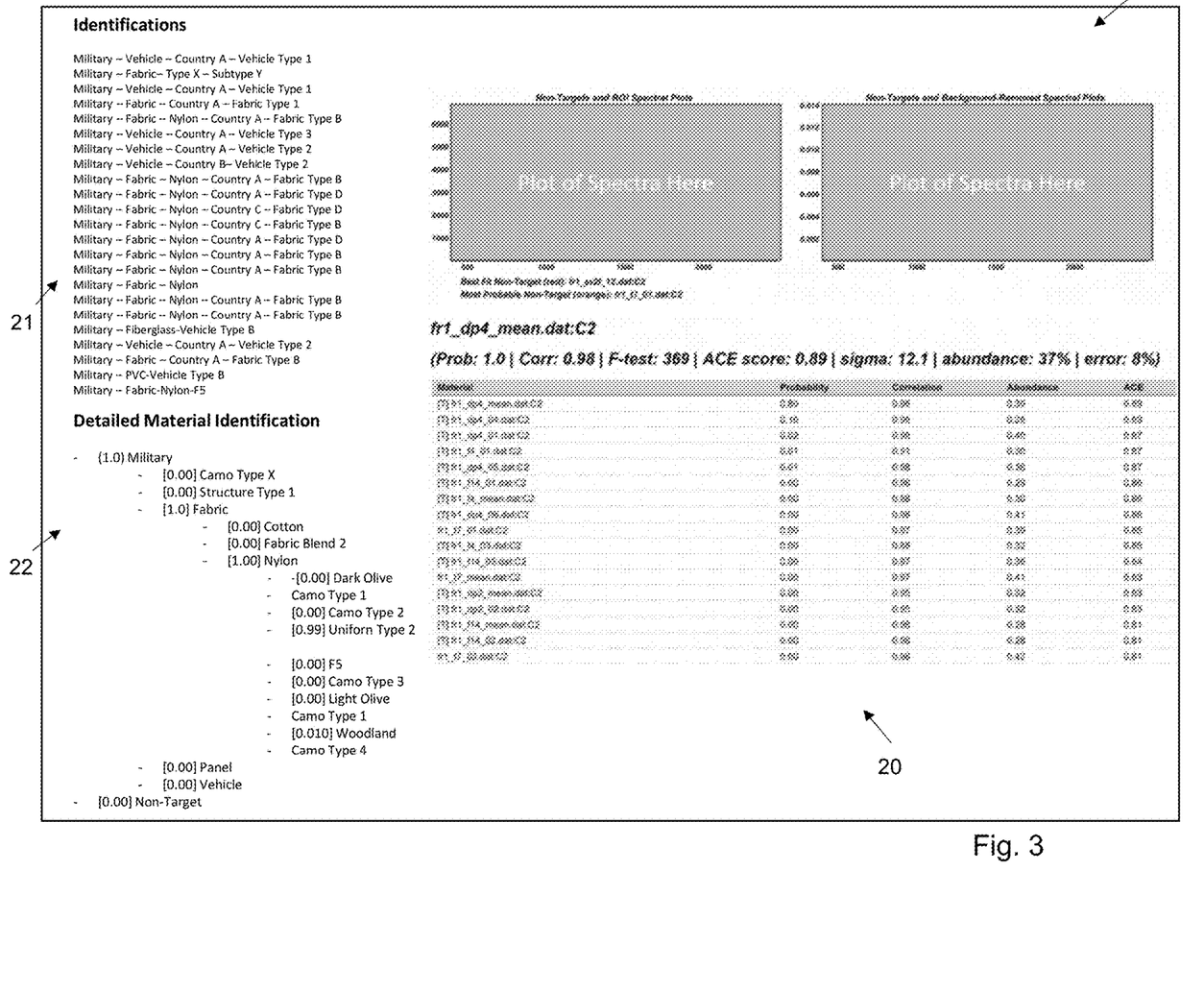
FIG. 3 is an exemplary output display in accordance with embodiments of the present disclosure.

A sample output from an automated processor executing software in accordance with the present disclosure is shown at 20 in FIG. 3. As can be seen therein, a list of identified objects is shown in the upper left column as at 21, and each object is given its series of top-probability material classes. The right-hand frame shows identification details as at 25 for an object whose first class is Military, second class is Fabric, third class is Nylon, and most specific class indicates the specific use for this type of nylon fabric ("Camo Type 2", which may serve as a replacement label for another term of more actionable meaning). The tree-diagram for this identification is provided as at 22 under "Detailed Material Identification" and the highest probability classes can be highlighted.

Previous methods only identify the material in a pixel by determining the set of materials present, or the presence or absence of a single target material of interest. The underlying statistics used in these methods (primarily likelihood ratio tests and linear regression methods) treat each library spectrum as a representative for a single material class and the statistics compute the likelihood for that class. For example, a red nylon spectrum determines the 'red nylon fabric' class. By using Bayesian model averaging regression with a hierchical library, the hierarchical identification method according to the present disclosure computes the probabilities of classes at multiple levels simultaneously, giving the probability of the material being a fabric, then the probability of a nylon fabric, then the specific red nylon fabric in the test. In various embodiments, software programming in accordance with the present disclosure can output the results in a collapsible tree user interface, such as at 22 in FIG. 2, or other visual display according to the requests and desires of the user.

The hierchical identification according to the present disclosure provides far more information than possible in previous methods. For some defense and security applications (e.g., counter-narcotics, improvised explosive devices, weapons of mass destruction), a material by itself has both innocent and undesired uses. Detection and identification of the presence of a material can be provided by previous methods, but hierchical identification can simultaneously and accurately determine if the suspect material has been prepared for nefarious use. As anther example using output shown in FIG. 3, nylon fabrics have many uses including military camaflouge materials. In accordance with the present disclosure, hierchical identification simultaneously matches the fabric with its specific use when possible.

The sequence of class designations for a hierchical identification is called the identification sequence. For example, the class sequence for the example shown at 22 in FIG. 2 is "Military—Fabric—Nylon—Camo Type 2". In a specific example associated with the output shown in FIG. 2, there are over three hundred different possible identification sequences, but each identified object need only be provided to the user with its sequence of at most four, greatly simplifying the user analysis.

Multi-Tier Target Library Processing

Modern automated hyperspectral imaging processing software includes a detection stage and an identification stage, as described, for example, in U.S. Pat. No. 8,897,489 to Basener, the disclosure of which is incorporated by reference herein in its entirety.

Software using the paradigm involving separate material detection and material identification steps involve a target library containing the spectra for target detection, and the same library spectra are used for identifying the target material in the identification stage. This now-standard paradigm seems logical because the target material is the same material for both detection and identification. The purpose of using a library of multiple target signatures, as opposed to a single spectrum for the target material, is that the library should capture variation(s) in the desired target. Including multiple target spectra in the library for each material allows for variation due to weathering, contaminants and other elements. For example, in searching for lost campers, one might use spectra for each of the anticipated plastic or nylon items the campers may have, such as coolers, tents, tarps, etc. Thus, one could easily have one hundred or more spectra.

The single target library used in past automated spectral imagery processing software is intended to include all variants of the target that are possible. The target material class is defined with all of its variations by the target library. However, some spectra for a target will have a high-false alarm rate in detection but are still useful in identification. For example, low abundance target spectra may have common confusers that lead to high false alarm rates in detection making them unsuitable for that purpose, but still must be included in identification for the identification at low abundances. Including them in spectral imagery processing software results in unacceptable high false alarm rates, but excluding them leaves some low abundance targets unidentifiable.

In addition, some spectra are needed for detection of materials in desired configurations, such as mixtures, for example. But, these spectra should not be included in the identification stage, as mixtures should be identified as mixtures of separate known library spectra of pure materials. Consider, for example, a military vehicle partially occluded by a nylon cover. A spectra from the vehicle alone would be unlikely to detect the nylon+vehicle mixed pixel, but a mixed spectra is suitable for this purpose.

In the multi-tier target library process according to the present disclosure, separate libraries for target detection are employed from those used for target identification in the identification stage. Using separate target libraries for detection and identification enables detection of mixtures and identification of low-abundance targets that are not possible with previous methods. This leads to significantly improved accuracy in both detection and identification.

Figure 4:
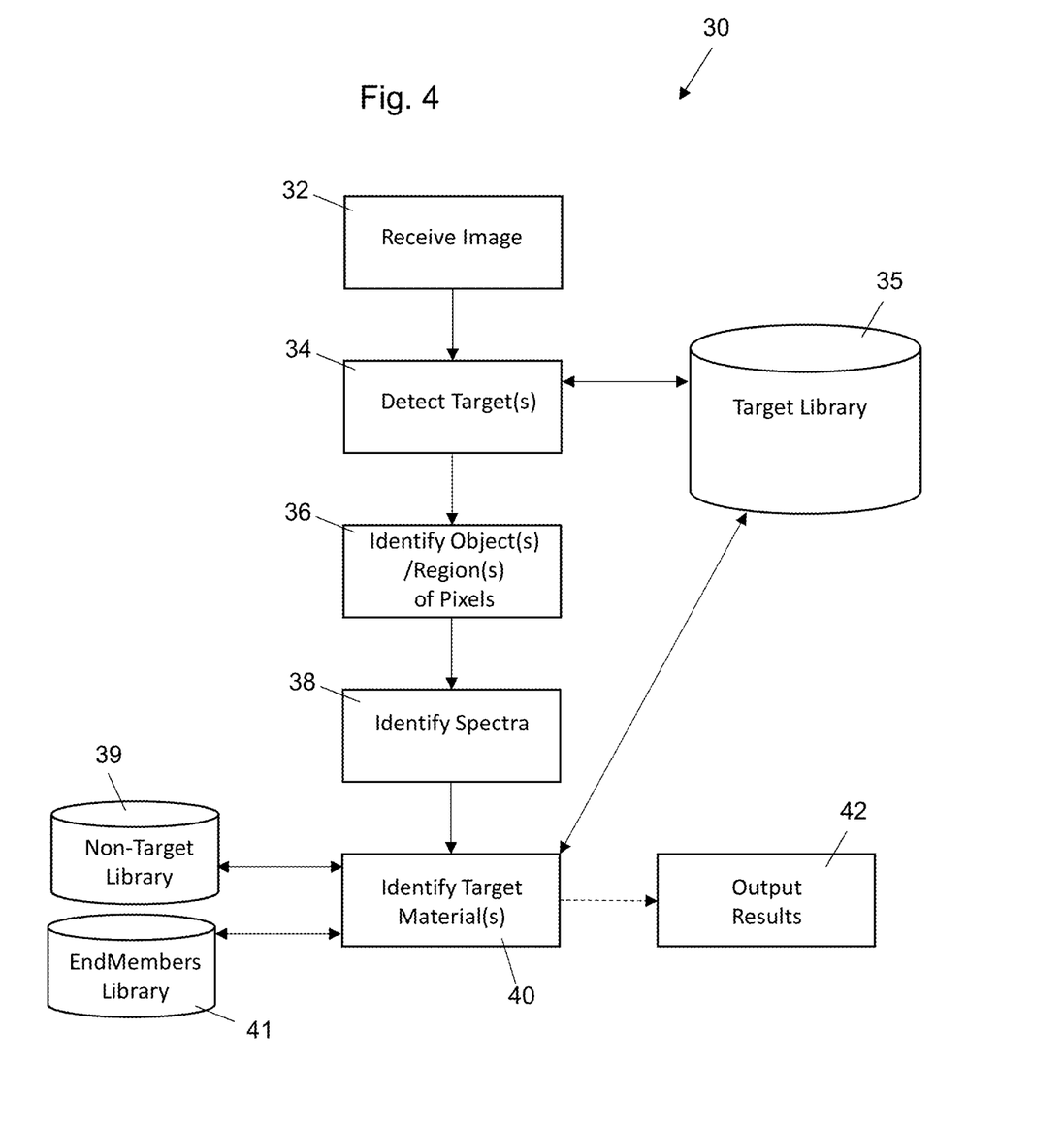
FIG. 4 is a process illustrating target identification from an image in accordance with embodiments of the present disclosure.

A flowchart illustrating an automated detection-identification framework with multi-tier library processing in accordance with the present disclosure is shown at 30 in FIG. 4. As shown at 32, a spectral image is received, and at 34, one or more targets are detected. The spectral image is made up of a number of image pixels. In detecting targets, a target detection library 35 is accessed to compare spectra with known models and/or signatures. The known models or signatures are stored as a first set of spectra for target materials. The target materials can be identified by multi-level hierarchical target material class designations, as illustrated in FIGS. 2A and 2B, for example.

As at step 36, a region or regions of pixels are selected based on the detected targets for the purpose of assessing the identities of the materials in the detected targets. In various embodiments, the region or regions of pixels can correspond to one or more objects of interest. In various embodiments, a single pixel is assessed. The selection in step 36 can be made by determining a target detection score representing the likelihood of presence of at least one of the target materials in each of the pixels in the spectral image. As at step 38, the spectra in the regions of pixels are identified, for example, based on the determined scores. As at step 40, the material(s) of the detected target(s) are identified, employing a non-target library 39 and an endmembers library 41 in accordance with various embodiments. The contents of the non-target library and endmembers library are part of a second set of spectra for target materials. The non-target library 39 and the endmembers library 41, individually or together, can be considered a target identification library. Additionally, the non-target library, endmembers library and portion of the target detection library can be considered another embodiment of a target identification library. The target identification library is employed to determine, by an apparatus as described herein, a material identification score representing a likely identification of one or more of the plurality of target materials for each region(s), pixel(s) and/or object(s) selected at step 36.

It will be appreciated that some target spectra are used for detection only and are stored in library 35, while a different subset of target spectra, such as spectra in the non-target database 39 and/or the endmember database 41, are used for identification. The detection-only spectra are typically mixtures of target with additional materials and the identification-only spectra are low abundance residues. It will further be appreciated that a subset of the first set of spectra stored in the target detection library can be the same as a subset of the second set of spectra stored in the target identification library. For example, the subset of the first set of spectra in the target detection library that does not include mixtures of target with additional materials may be common as among the first and second sets of spectra.

The identification step 40 can employ a regression method such as model averaging to work with mixture models of pure spectra, and the additional non-target materials that are likely to be mixed with target are provided to the identification stage in an endmembers library 41, for example. Optionally, the identified materials from step 40 can be output in various forms as at 42, such as through a display on a computing device, for example.

It will be appreciated that the target detection score for each of the pixels can be determined simultaneously, and the material identification score for each of the pixels can be determined simultaneously. Further, the material identification score can determined simultaneously for each multi-level hierarchical target material class designation provided. Thus, for example, if material is categorized in a hierarchy of Military—Fabric—Nylon—Uniform Type 2 as in FIG. 3, embodiments of the present disclosure can simultaneously determine the material identification scores for Military and Non-Target (at level one, for example), Fabric, Structure, Panel and Vehicle (at level two, for example), Cotton, Fabric Blend and Nylon (at level three, for example) and Dark Olive, Camo Type 1, Uniform Type 1, etc. (at level four, for example). In this way, rapid evaluation and identification of material(s) is accomplished.

As a practical example, consider the use of hyperspectral imagery to detect and identity illicit cocaine production. Processes for producing cocaine from cocoa leaves are available online, and generally involve a sequence of events. At various stages in various processes, the cocoa leaves are mixed with lime, kerosene, sulfuric acid, potassium permanganate, and much of the processing involves laying the leaves in the open on large plastic tarps.

Automated hyperspectral processing software that defines target materials by a single library would be unlikely to detect the cocaine processing if the target library were cocoa leaves alone, and would have an extremely high false alarm rate in identification if the library contained spectra from all combinations of cocoa with lime, kerosene, sulfuric acid, potassium permanganate, and plastic tarps. However, software using the multi-tier target library process according to the present disclosure can detect the potential mixtures and properly separate out the mixtures into constituents in the identification stage. Spectra collected from the mixtures of coca leaf with additional materials would be used for detection, the cocoa only would be used as a target in identification, and the additional materials would be used as endmembers.

It is known that producing coca paste can involve the use of plastic tanks, cement mixers, nylon tarps and other materials. While the open layout of the leaves in plastic tanks and nylon tarps would be visible to overhead imagery, only processing the imagery using multi-tier library processing as described in the present disclosure detects and identifies the materials needed to determine the illicit activity.

Linear Mixing and Regression

In the ideal, each pixel in a hyperspectral image contains light that has reflected from (or emitted from) multiple different materials, and the resulting measured spectrum is the sum of the spectra for each constituent material multiplied by the percentage of incident light that reflected off that material. The assumption that the measured spectrum in a pixel is a linear combination of the individual material spectra is called the linear mixing model. Although there are additional factors that can be considered, the linear mixing model is the theoretical foundation of target detection and identification algorithms.

Mathematically, the linear mixing model assumes that the observed spectrum x is approximately equal to the sum of the products of the abundance coefficients $c_i$ (a scalars) and individual material spectra $s_i$ (vectors):

$$x \approx \sum_i c_i s_i$$

Each $s_i$ is a spectrum of a known material and the coefficient $c_i$ is the percent of measured light in the pixel coming from this material.

Given a pixel spectrum x and a library of spectra from known materials, the process of determining the materials $s_i$ from the library and associated abundances $c_i$ that can be combined to obtain the measured spectrum is called unmixing. If a set of known spectra is found whose linear combination results in the measured spectrum, then a likely set of materials present in the pixel has been identified.

More generally, the process of taking an observed (e.g., dependent) vector and underlying (e.g., independent) variables is called regression, and when the relationship is that of a linear combination as in the linear mixing model, the process is called linear regression. Standard regression algorithms/software attempt to choose the best possible model out of the many possible combinations. Here, "best" usually means the model with the lowest error in approximating x while penalizing models based on the number of elements in the models.

With regard to material identification, while the detection of known targets is possible even at low abundances, target detection algorithms have a tendency to score high on materials that are similar to targets but are not targets. These similar-to-target materials are called confusers, and a high score on a confuser is called a false alarm for the detection algorithm.

Two-Stage Identification

As noted above, by employing two-stage identification, the system, method and apparatus of the present disclosure provides a statistically rigorous method that, in various embodiments, uses a model selection metric such as an F-Test to screen models that are not sufficiently good in comparison to the null model specifically to determine if spectra in the library are sufficient to model the image pixel. Only models with a sufficiently high F-test or other model score are used in model averaging to distinguish between targets and hard confusers. The F-test, or other model, scores and model averaging metrics are then combined in the final confidence for the identification. For example, a low F-test score indicates that the material(s) present in the image spectrum are not in the library, and thus the library is incomplete and the model averaging results should be discarded and/or rejected. As a further example, a high F-test score indicates that the materials in the image spectrum are present, and the model averaging can be used. In this example, a sliding scale between high and low F-test scores is determined, and for moderate F-test scores the model averaging results can be used but with a confidence provided to the user that is proportional to the F-test score. In these ways, the best qualities of the F-test based or other model-based methods and model averaging methods are provided, and in a single mathematical framework has a low false alarm rate on materials not present in the libraries, and has the effectiveness of model averaging to distinguish targets from confusers.

The two-stage process involving detection and then identification can exclude false alarms on confusers. In this process, including a detection step and an identification step, a target detection algorithm can be run to obtain detection planes, high-scoring pixels from the planes can be chosen, further identification algorithms to the high scoring pixel and local region can be applied, and then a list of results that can be sorted by the scores from the identification process is produced, such as illustrated, for example, in FIG. 4. This approach is object-based in the sense that the user examines a list of regions in the image with information about the object in each region, instead of pixel-based, with the user visually examining the scores in detection planes for each pixel.

The identification includes a regression using a library of target spectra, called the target library, and endmembers from the image.

As noted above, identification using linear mixing is determining the materials present in the best possible model, which is a standard regression process. Also noted above, the most common metric for measuring the goodness of a model in hyperspectral imaging is the F-test, which is mathematically the product of a term measuring the error in the model times a term dependent on the number of elements in the model. The F-test is a standard statistical metric invented by R. A. Fisher.

While the F-test is a reliable method for picking a best model, evaluating the viability of that model, it has known limitations. One of the biggest limitations is that there may be models that are nearly as good as the best one, and these get ignored by the F-Test pick-a-winner approach. Model averaging is a regression method in which the goal is not to determine the single best model, but a collection of good models and average results of this set of good models.

Past processes using the model averaging approach described selecting a region of interest from the image, estimated to be tens to hundreds of pixels, and determining a spectral library of chemicals for identification, estimated to included one hundred or more chemicals. In model averaging, a model search space is determined, which is the set of all models that will be used. For each model in the model search space, regression coefficients are computed for the materials in the model, and then the likelihood for that model is computed. The likelihoods for all models in the search space are combined to determine the desired probabilities.

Two methods tested for building a model search space included Occam's Window and the Leaps Algorithm:

Model Selection

If the null model, all single-chemical models, all paired-chemical models, and all triple-chemical models are allowed, there are $$M = \binom{p_{Lib}}{0} + \binom{p_{Lib}}{1} + \binom{p_{Lib}}{2} + \binom{p_{Lib}}{3} \text{ models}$$

The probability that a given chemical is present in the region is determined as the cumulative sum of probabilities of all models that contain the spectrum from that chemical.

$P(C_j) = \Sigma_{i=1}^{M}(Cj \epsilon Mi)P(Mi)$, where $I(\ )$ equals 1 if its argument is true.

In various embodiments, a tunable threshold is selected, such as T=0.90, and predict that chemical j is present if $P(C_j)$ exceeds T. The presence of the chemical is determined if the cumulative probability $P(C_j)$ exceeds a chosen threshold T.

An advantage of model averaging is that it provides information from multiple top models instead of trying to find a single "correct" model. Prior to the two-tier identification combining both F-test methods and model averaging as disclosed herein, one had to evaluate the trade-off between the two methods.

It will thus be appreciated that the present disclosure provides embodiments for improving material identification in hyperspectral imagery through a system, method and apparatus incorporating hierarchical identification, multi-tier target libraries and two-stage identification as described herein. The hierarchical identification provides a far richer form of identification, as hundreds of classes can be identified simultaneously. The hierarchical identification further provides the ability to distinguish between similar target classes. The multi-tier target library process provides more accurate detections and identification on target materials, especially at low abundances, mixtures of materials, and in unusual configurations. The two-stage identification provides the ability of model averaging identification methods to distinguish between targets and confusers in combination with the F-test advantages of evaluating which models are truly viable to mitigate against cases where the material in an image is not in the libraries.

Figure 5:
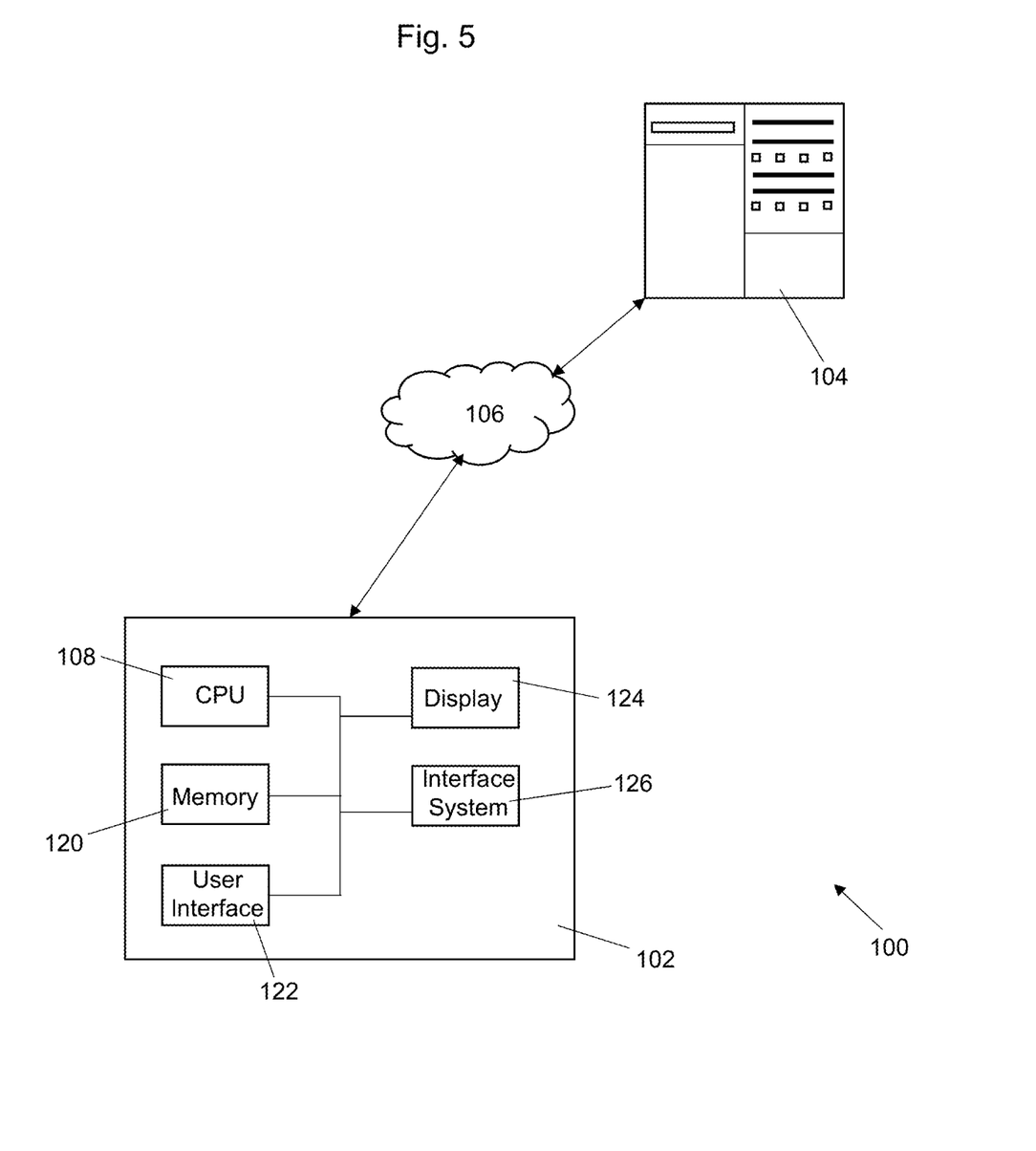
FIG. 5 is a diagram of a system in accordance with embodiments of the present disclosure.

An environment 100 with an exemplary target detection and material identification processing apparatus 102 is illustrated in FIG. 5. The environment 100 includes the apparatus 102 and an image and target signature library server 104 coupled together by a communications network 106, although the environment can comprise other types and numbers of systems, devices, networks, and elements in other configurations. In various embodiments, server 104 can provide a target detection database or library (such as library 35 in FIG. 4), a non-target library (such as library 39 in FIG. 4) and endmember library (such as library 41 in FIG. 4). This provides a number of advantages including providing a more efficient, effective and automated method for object-based sorting and ranking of target detections.

The target detection and material identification processing apparatus 102 can include at least one processor 108, at least one memory storage device 120, at least one user interface 122, at least one display 124, and at least one interface system 126 which are coupled together by bus or other link, although the device may comprise other types and numbers of elements in other configurations. In various embodiments, the user interface 122 and display 124 can be the same device.

The processor(s) 108 in the apparatus 102 executes a program of stored instructions for one or more aspects of the present disclosure as described and illustrated herein, although the processor could execute other numbers and types of programmed instructions. The memory storage device(s) 120 in the apparatus 102 stores these programmed instructions for one or more aspects of the present invention as described and illustrated herein, although some or all of the programmed instructions could be stored and/or executed elsewhere. A variety of different types of memory storage devices, such as a random access memory (RAM) or a read only memory (ROM) in the system or a floppy disk, hard disk, CD ROM, or other computer readable medium which is read from and/or written to by a magnetic, optical, or other reading and/or writing system that is coupled to the processor(s) 108 in the apparatus 102 can be used for the memory storage device(s) 120 in the apparatus 102.

The user interface(s) 122 in the apparatus 102 is used to input selections and data, although the user input device could be used to input other types of information and interact with other elements. The user interface(s) 122 can include a computer keyboard and a computer mouse, although other types and numbers of user input devices can be used.

The display(s) 124 in the apparatus 102 is used to show images and other information to the user. The display(s) 124 can include a computer display screen, such as a CRT or LCD screen, although other types and numbers of displays could be used.

The interface system 126 is used to operatively couple and communicate between the apparatus 102 and the image and target signature library server 104 over the communication network 106, although other types and numbers of communication networks or systems with other types and numbers of connections and configurations to other types and numbers of systems, devices, and components can be used. By way of example only, the communication network can use TCP/IP over Ethernet and industry-standard protocols, including SOAP, XML, LDAP, and SNMP, although other types and numbers of communication networks, such as a direct connection, a local area network, a wide area network, modems and phone lines, e-mail, and wireless communication technology, each having their own communications protocols, can be used.

In various embodiments, the image and target signature library server 104 includes a central processing unit (CPU) or processor, a memory, and an interface or I/O system, which are coupled together by a bus or other link, although other numbers and types of network devices could be used. For example, the target signatures could be stored in other types of storage or computing devices and the images could be obtained directly from image capture sensors or other storage devices. Generally, in this example the image and target signature library server 104 processes requests received from the apparatus 102 via communication network 106 for images and signatures, although other types of requests for other types of data could be processed. The image and target signature library server 104 may provide data or receive data in response to requests from the apparatus 102.

Although the apparatus 102 and image and target signature library server 104 are described and illustrated herein, other types and numbers of systems, devices, components, and elements in other topologies can be used. It is to be understood that the systems of the examples described herein are for exemplary purposes, as many variations of the specific hardware and software used to implement the examples are possible, as will be appreciated by those skilled in the relevant art(s).

In addition, two or more computing systems or devices can be substituted for any one of the systems in any example. Accordingly, principles and advantages of distributed processing, such as redundancy and replication also can be implemented, as desired, to increase the robustness and performance of the devices and systems of the examples. The examples may also be implemented on computer system or systems that extend across any suitable network using any suitable interface mechanisms and communications technologies, including by way of example only telecommunications in any suitable form (e.g., voice and modem), wireless communications media, wireless communications networks, cellular communications networks, G3 communications networks, Public Switched Telephone Network (PSTNs), Packet Data Networks (PDNs), the Internet, intranets, and combinations thereof.

The examples may also be embodied as non-transitory computer readable medium having instructions stored thereon for one or more aspects of the technology as described and illustrated by way of the examples herein, which when executed by a processor (or configurable hardware), cause the processor to carry out the steps necessary to implement the methods of the examples, as described and illustrated herein. Common forms of computer-readable media that may be used in the performance of the present invention include, but are not limited to, floppy disks, flexible disks, hard disks, magnetic tape, any other magnetic medium, CD-ROMs, DVDs, any other optical medium, punch cards, paper tape, any other physical medium with patterns of holes, RAM, PROM, EPROM, FLASH-EEPROM, any other memory chip or cartridge, or any other medium from which a computer can read. The term "computer-readable medium" when used in the present disclosure can refer to any medium that participates in providing data (e.g., instructions) that may be read by a computer, a processor or a like device. Such a medium can exist in many forms, including, for example, non-volatile media, volatile media, and transmission media. Non-volatile media include, for example, optical or magnetic disks and other persistent memory. Volatile media can include dynamic random access memory (DRAM), which typically constitutes the main memory. Transmission media may include coaxial cables, copper wire and fiber optics, including the wires or other pathways that comprise a system bus coupled to the processor. Transmission media may include or convey acoustic waves, light waves and electromagnetic emissions, such as those generated during radio frequency (RF) and infrared (IR) data communications.

Unless otherwise stated, devices or components of the present invention that are in communication with each other do not need to be in continuous communication with each other. Further, devices or components in communication with other devices or components can communicate directly or indirectly through one or more intermediate devices, components or other intermediaries. Further, descriptions of embodiments of the present invention herein wherein several devices and/or components are described as being in communication with one another do not imply that all such components are required, or that each of the disclosed components must communicate with every other component. In addition, while algorithms, process steps and/or method steps may be described in a sequential order, such approaches can be configured to work in different orders. In other words, any ordering of steps described herein does not, standing alone, dictate that the steps be performed in that order. The steps associated with methods and/or processes as described herein can be performed in any order practical. Additionally, some steps can be performed simultaneously or substantially simultaneously despite being described or implied as occurring non-simultaneously.

It will be appreciated that algorithms, method steps and process steps described herein can be implemented by appropriately programmed general purpose computers and computing devices, for example. In this regard, a processor (e.g., a microprocessor or controller device) receives instructions from a memory or like storage device that contains and/or stores the instructions, and the processor executes those instructions, thereby performing a process defined by those instructions. Further, programs that implement such methods and algorithms can be stored and transmitted using a variety of known media.

Where databases are described in the present disclosure, it should be appreciated that alternative database structures to those described, as well as other memory structures besides databases may be readily employed. The drawing figure representations and accompanying descriptions of any exemplary databases presented herein are illustrative and not restrictive arrangements for stored representations of data. Further, any exemplary entries of tables and parameter data represent example information only, and, despite any depiction of the databases as tables, other formats (including relational databases, object-based models and/or distributed databases) can be used to store, process and otherwise manipulate the data types described herein. Electronic storage can be local or remote storage, as will be understood to those skilled in the art.

It will be apparent to one skilled in the art that any computer system that includes suitable programming means for operating in accordance with the disclosed methods also falls well within the scope of the present disclosure. Suitable programming means include any means for directing a computer system to execute the steps of the system and method of the invention, including for example, systems comprised of processing units and arithmetic-logic circuits coupled to computer memory, which systems have the capability of storing in computer memory, which computer memory includes electronic circuits configured to store data and program instructions, with programmed steps of the method of the invention for execution by a processing unit. Aspects of the present invention may be embodied in a computer program product, such as a diskette or other recording medium, for use with any suitable data processing system. The present invention can further run on a variety of platforms, including Microsoft Windows™, Linux™, MacOS™, iOS™, Android™, Sun Solaris™, HP/UX™, IBM AIX™ and Java compliant platforms, for example. Appropriate hardware, software and programming for carrying out computer instructions between the different elements and components of the present invention are provided.

The present disclosure describes embodiments of the present approach, and these embodiments are presented for illustrative purposes only. These embodiments are described in sufficient detail to enable those skilled in the art to practice the present approach, and it will be appreciated that other embodiments may be employed and that structural, logical, software, electrical and other changes may be made without departing from the scope or spirit of the present invention. Accordingly, those skilled in the art will recognize that the present approach may be practiced with various modifications and alterations. Although particular features of the present approach can be described with reference to one or more particular embodiments that form a part of the present disclosure, and in which are shown, by way of illustration, specific embodiments of the present approach, it will be appreciated that such features are not limited to usage in the one or more particular embodiments or figures with reference to which they are described. The present disclosure is thus neither a literal description of all embodiments nor a listing of features that must be present in all embodiments.

The present approach may be embodied in other specific forms without departing from the spirit or essential characteristics thereof. The present embodiments are therefore to be considered in all respects as illustrative and not restrictive, the scope of the invention being indicated by the claims of the application rather than by the foregoing description, and all changes which come within the meaning and range of equivalency of the claims are therefore intended to be embraced therein.

The invention claimed is:

1. A method for detection and identification of target material in spectral imagery, comprising:
    storing a first set of spectra for a plurality of target materials in a target detection library;
    receiving a spectral image captured by and transmitted from an image capture sensor;
    determining, by an apparatus using the target detection library, a target detection score representing the likelihood of presence of at least one of the plurality of target materials in each of a plurality of pixels in the spectral image;
    storing a second set of spectra for the plurality of target materials in a target identification library;
    determining, by the apparatus using the target identification library, a material identification score representing a likely identification of one or more of the plurality of target materials for each of the plurality of pixels, wherein the material identification score is determined as a set of probabilities with a probability for each class label at each level in a multi-level hierarchical target material class designation; and
    based on the material identification score, identifying and displaying a target material on a display.

2. The method of claim 1, wherein the target identification library comprises a non-target library and an endmember library.

3. The method of claim 2, wherein the first set of spectra comprises at least one mixture of one or more of the target materials with at least one additional non-target material.

4. The method of claim 2, wherein the second set of spectra comprises at least one low abundance target material.

5. The method of claim 1, wherein a subset of the first set of spectra stored in the target detection library is the same as a subset of the second set of spectra stored in the target identification library.

6. The method of claim 1, wherein the target detection score for each of the plurality of pixels is determined simultaneously, and wherein the material identification score for each of the plurality of pixels is determined simultaneously.

7. The method of claim 1, wherein each of the plurality of target materials comprises a respective class designation from a plurality of multi-level hierarchical target material class designations, and wherein the material identification score is determined simultaneously for each of the plurality of multi-level hierarchical target material class designations.

8. The method of claim 1, further comprising determining the first set of spectra and the second set of spectra.

9. The method of claim 1, wherein determining a material identification score comprises determining a model selection metric for each of a plurality of linear mixture models and applying model averaging on the plurality of linear mixture models.

10. The method of claim 9, wherein determining a material identification score further comprises, after determining the model selection metrics for each of the plurality of linear mixture models, rejecting one or more of the plurality of linear mixture models.

11. An apparatus for detecting and identifying target material in spectral imagery, comprising:
an image capture sensor;
at least one processor;
at least one memory device storing a plurality of instructions which, when executed by the at least one processor, cause the at least one processor to:
determine, using a target identification library, a material identification score representing a likely identification of one or more of a plurality of target materials for each of a plurality of pixels in a spectral image obtained from the image capture sensor, wherein the material identification score is determined as a set of probabilities with a probability for each class label at each level in a multi-level hierarchical target material class designation; and
based on the material identification score, identifying and displaying a target material on a display.

12. The apparatus of claim 11, wherein the target identification library comprises a non-target library and an end-member library.

13. The apparatus of claim 12, wherein the instructions cause the at least one processor to determine, using a target detection library comprising a first set of spectra, a target detection score representing the likelihood of presence of at least one of a plurality of target materials in each of a plurality of pixels in a spectral image, and wherein the first set of spectra comprises at least one mixture of one or more of the plurality of target materials with at least one additional non-target material.

14. The apparatus of claim 12, wherein the target identification library comprises a set of spectra comprising at least one low abundance target material.

15. The apparatus of claim 11, wherein each of the plurality of target materials comprises a respective class designation from a plurality of multi-level hierarchical target material class designations, and wherein the material identification score is determined simultaneously for each of the plurality of multi-level hierarchical target material class designations.

16. The apparatus of claim 11, wherein the plurality of instructions further cause the at least one processor to determine a model selection metric for each of a plurality of linear mixture models and apply model averaging on the plurality of linear mixture models.

17. A system for detection and identification of target material in spectral imagery, comprising:
an image capture sensor;
an apparatus comprising at least one processor and at least one memory device storing a plurality of instructions which, when executed by the at least one processor, cause the at least one processor to:
establish a plurality of multi-level hierarchical target material class designations for a plurality of target materials;
receive at least one spectral image from the image capture sensor, wherein the at least one spectral image comprises a plurality of pixels;
determine, using a target identification library, a material identification score representing a likely identification of one or more of the plurality of target materials for the at least one pixel, wherein the material identification score is determined as a set of probabilities with a probability for each class label at each level in a multi-level hierarchical target material class designation; and
an interface in communication with the at least one processor representing the material identification score and an identification of one or more of the plurality of target materials for the at least one pixel.

18. The system of claim 17, wherein the plurality of instructions cause the at least one processor to simultaneously determine the material identification score for each of the plurality of multi-level hierarchical target material class designations.

19. The system of claim 17, wherein the plurality of instructions further cause the at least one processor to determine a model selection metric for each of a plurality of linear mixture models and apply model averaging on the plurality of linear mixture models.

20. The system of claim 17, wherein a first set of spectra for a plurality of target materials is stored in the target detection library, a second set of spectra for a plurality of target materials is stored in the target identification library, and the first set of spectra is different from the second set of spectra.

* * * * *